United States Patent [19]

Huck et al.

[11] Patent Number: 4,574,948
[45] Date of Patent: Mar. 11, 1986

[54] LINEAR FOLD ARMED SUTURE

[75] Inventors: Charles M. Huck, Pottersville; Charles R. Ashley, Clinton, both of N.J.

[73] Assignee: Howmedica, Inc., New York, N.Y.

[21] Appl. No.: 676,602

[22] Filed: Dec. 3, 1984

Related U.S. Application Data

[63] Continuation of Ser. No. 241,107, Mar. 6, 1981, abandoned.

[51] Int. Cl.$^4$ ................. A61L 17/02; B65D 75/04
[52] U.S. Cl. .................... 206/63.3; 206/363; 206/380
[58] Field of Search ............ 206/63.3, 277, 363, 206/380, 382, 383, 388, 476, 477, 484, 484.1, 484.2

[56] References Cited

U.S. PATENT DOCUMENTS 3,500,998  3/1970  Sanders ............... 206/382
4,412,613 11/1983  Kubas ................. 206/63.3

Primary Examiner—George E. Lowrance
Assistant Examiner—Jimmy G. Foster
Attorney, Agent, or Firm—Pennie & Edmonds

[57] ABSTRACT

A device for storing and dispensing a suture includes an outer envelope formed of two panel layers which are sealed along their peripheries so as to hermetically enclose a region therebetween. An inner container positioned within the region includes a rectangular center panel which has a pocket formed by an overlaying window to snugly retain a needle therein. A second panel foldably secured to one longitudinal edge of the center panel receives on its left-half the major portion of the suture. The right-half of the side panel is then folded over the suture and again is folded over onto the upper surface of the center panel. A tab formed of the center panel is provided so as to lock the side panel when positioned on the center panel. A window is provided in the upper panel layer and overlies the window of the center panel so that the needle and a portion of the thread are viewable therethrough. After tearing or removing a portion of the two panel layers so as to expose the window on the center panel, the envelope and center panel are folded in half so as to expose a portion of the needle together with a portion of the suture free of the surface of the center panel. The center panel has a score line centrally positioned along the longitudinal axis thereof to aid in the folding of the center panel. A method for storing and dispensing the suture and respective needle is also disclosed.

35 Claims, 6 Drawing Figures

LINEAR FOLD ARMED SUTURE

This is a continuation of application Ser. No. 241,107, filed Mar. 6, 1981, now abandoned.

TECHNICAL FIELD

The present invention relates to a device for storing a suture prior to its use and, particularly, to a container providing a sterile environment while permitting ease of dispensing the suture when required.

BACKGROUND ART

It is well known to employ sutures for the purpose of closing a wound or an incision created during an operation. For this reason, it is necessary that the suture be maintained in a sterile condition at all times prior to its use. Moreover, it is also necessary that the suture be readily available when needed so as to permit efficient and expeditious use thereof.

Typically, sutures are known which are contained in packages so as to preserve the sterile condition of the sutures. Such packages typically provide suitable arrangement of the sutures so as to prevent any entangling of the sutures upon their removal from the package. Such known sutures and their accompanying packages are described in U.S. Pat. Nos. 3,280,971; 3,939,969; 4,063,638; and 4,069,912.

Each of these patents relates to a suture package which contains sutures in a sterile condition prior to use. The '971 patent relates to a suture package intended to retain the suture strands in such a way that they can be removed easily from the package and will not be kinked or bent upon removal. The '971 patent package includes a coiled hollow restraining tube which is retained within a holding sleeve formed from a sterilizable stiff sheet material. The tube is large enough so that a plurality of sutures can be contained therein in a loose fashion and furthermore so that they do not entangle with one another during their storage. Outside of the tube, the sutures at their free end are attached to individual curved needles which are permitted to rest loosely in an unconstrained fashion upon the sheet material.

The '969 patent discloses a suture package including a suture retainer made up of three panels. The suture strand is coiled and placed upon a middle panel while the needle is curved back and superimposed over a second panel which in turn overlies the first panel. Moreover, a third panel thereafter overlies the second panel and thereby covers the needle itself. The third panel itself includes a tab at an end portion which upon being pulled away from the third panel permits separation along a tear line so as to expose the suture needle laying upon the second panel.

The '638 patent relates to a suture package also including an inner envelope consisting of three connected panels. As was the case in the '969 patent, the suture strand is placed or retained in a non-entangling configuration upon the second panel which may include strand retainers if desired. One of the end panels along this upper peripheral edge includes a series of perforations and slits extending therefrom to the peripheral edge so as to receive and retain an end portion of the strand. The needle which is attached to the end of the respective strand in turn is placed upon an end panel and is retained thereon by inserting the needle end through a slit provided in the end panel.

Similarly, the '912 patent also relates to a suture package wherein the needle attached to a suture surgical strand is retained underneath an overlapping panel of a suture label by inserting the needle through a slit contained in an overlapping panel portion. Accordingly, only a small portion of the needle is exposed and available for securing with a suitable device for removal of the needle therefrom.

Notwithstanding the improvements which the above-identified patents offer with respect to packages suitable for containing sutures in a sterile condition prior to use, these devices still present difficulties with which the operating personnel must cope.

Most of the presently known suture packages retain the needle portion of the suture in a flat abutting relationship with the packaging material itself. For this reason, removal of the suture is made difficult inasmuch as the needle lies flat against a panel. Typically, a nurse or surgeon is required to dig into the package to get at the needle. This problem is further complicated when dull needle holders are employed. In addition, none of the above-identified suture packages provide for arming from the pack or container either for right or left-handed suturing. Oftentimes, it is necessary for the nurse or surgeon to employ the needle holder as a removal tool since the needle is oftentimes buried in the package and thereafter in a subsequent step to reposition the needle in accordance with the surgeon's needs. For this reason, the suture packages described above do not present an armed suture which is physically convenient and readily viewable prior to use. Also, it is known in typical suture packages that the needle migrates out of its planned or intended location. As a result, the needle may not be found where expected and further searching within the suture package is required. This further complicates the process of removing the needle and suture from the package itself.

Such difficulties also involve the limited visibility which these patented devices provide with respect to the suture and their respective needles. Limited visibility does not permit an easy and efficient determination of the needle count and the product style prior to opening the package itself.

In addition, it is desirable to obtain efficient economy of use which results from not opening the wrong package. Such is the case where the package cover itself totally encloses the inner suture container and for this reason prevents the viewing of the type of suture enclosed. Moreover, it is desirable to permit viewing of the suture while within the container and thereby determine the true characteristics of the suture within without relying upon a two-dimensional description or illustration presented on the package cover.

DISCLOSURE OF THE INVENTION

The present invention relates to a container for dispensing at least one suture secured to one end of a needle, comprising first panel means for retaining a portion of the needle, the first panel means capable of being folded along a predetermined axis such that the remaining portion of the needle is exposed free of the first panel means upon folding of the first panel means along the predetermined axis, and second panel means for retaining a major portion of the suture, the second panel means being connected to the first panel means and configured such that the suture can be withdrawn therefrom upon removal of the needle from the first panel means.

In a preferred embodiment, the present invention relates to a container for dispensing a suture secured to one end of a needle, comprising first panel means for securely retaining a portion of the needle, the first panel means capable of being folded along a predetermined axis in the plane of the first panel means such that the remaining portion of the needle is exposed free of the first panel means upon folding of the first panel means along the predetermined axis, and second panel means for securely retaining a major portion of the suture, the second panel means being connected to the first panel means and configured such that the suture can be withdrawn therefrom upon removal of the needle from the first panel means. The first panel means includes a window portion permitting viewing of the needle retained in secured relationship with the first panel means. Preferably, the window portion is constructed of transparent material and the first and the second panel means are of a generally rectangular configuration.

The first and second panel means are foldably secured to each other along respective longitudinal edges thereof. The longitudinal edges are aligned with the predetermined axis. Accordingly, the second panel means is capable of being folded along its longitudinal axis such that the second panel means encloses the major portion of the suture thread upon folding of the second panel means back upon itself along its longitudinal axis. The second panel means includes a tab portion extending outwardly from a peripheral edge thereof. The tab is capable of being folded back onto the second panel means so as to guide the major portion of the suture during its withdrawal from the second panel means.

In its folded condition enclosing the major portion of the suture, the second panel means is folded over along its longitudinal edge connected to the first panel means so as to overlap a surface portion of the first panel means. The first panel means includes a means for securing the second panel means when placed in overlapping relationship therewith.

According to one embodiment, the securing means is a tab centrally positioned on the first panel means so as to overlie at least a portion of and secure the second panel means. In an alternative embodiment, the container further includes a third panel means foldably secured along one longitudinal edge to the other longitudinal edge of the first panel means. Also, an aperture is positioned centrally of the first panel means and a tab is centrally formed of the third panel means such that upon folding of the third panel means onto the surface of the first panel means opposite the second panel means, the tab can be extended through the aperture so as to overlie at least a portion of and secure the second panel means.

Preferably, each of the panel means are integrally constructed of a bleached sulphite board. The second panel means, if desired, also includes means for maintaining the major portion of the suture in a predetermined configuration so as to prevent entangling or kinking of the major portion of the suture during dispensing of the suture therefrom. It is preferred that the panel means are capable of being sterilized by at least one of irradition and ethylene oxide sterilizing methods.

The present invention also relates to a device for storing and dispensing a suture secured to one end of a needle, comprising outer container means including a first panel layer and a second panel layer of like configuration and dimension, the first and second panel layers being secured together along their peripheries so as to define an enclosed region therebetween, the first panel layer including a first window portion permitting viewing of the enclosed region. The device also comprises inner container means positioned within said region which includes first panel means and second panel means as described hereinabove. The first panel means includes a second window portion permitting viewing of the needle retained in secured relationship with said first panel means. Preferably, the first window portion is of a larger surface dimension than the second window portion such that the first window portion can overlie the second window portion so as to permit viewing of the entire needle together with at least a portion of the suture through the first and second window portions.

The first panel layer and the second panel layer each include a similarly positioned notch so as to permit tearing and removal of the first and second panel layers adjacent the first window portion. The first and second panel layers are each of a generally rectangular configuration and are constructed of a clear polyester capable of being imprinted so as to provide numerical and identifying indicia thereon. If desired, the second panel layer includes a layer of metallic foil. Also, the first and the second panel layers are capable of being sterilized by at least one of irradition and ethylene oxide sterilizing methods.

The first and the second panel means are also of a generally rectangular configuration and are configured and dimensioned so as to be capable of being enclosed within the region defined between the first and the second panel layers. Preferably, the corner of the first panel means adjacent the second window is generally curvilinearly configured such that the second layer panel upon being torn apart adjacent the first window portion separates along the curvilinear configuration.

The present invention also relates to a method of dispensing a suture secured to one end of a needle, comprising taking a device for storing and dispensing a suture and needle as described hereinabove, tearing a portion of the first and the second panel layers away therefrom so as to expose the needle and at least a portion of the suture connected thereto, folding said device along a predetermined axis, and withdrawing the needle from the second window portion and thereafter withdrawing the suture from the inner container.

BRIEF DESCRIPTION OF THE DRAWINGS

The present invention is described in detail below herein with reference to the drawings in which.

BEST MODE FOR CARRYING OUT THE INVENTION

Figure 1:
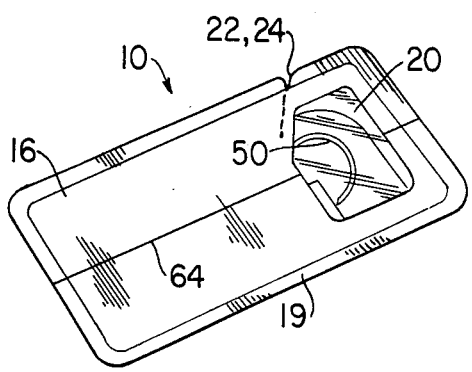
FIG. 1 is a perspective view illustrating a suture package according to the present invention in a sealed condition ready for use.

In the description which follows, any reference to either orientation or direction is intended primarily for the purpose of illustration and is not intended in any way as a limitation of the scope of the present invention.

Referring to the drawings, a device or suture package 10 is illustrated according to the present invention for storing and dispensing an armed suture. As used herein, the term "armed suture" is meant to include surgical strands used for suturing, ligating and the like which includes at least one needle attached to one end of the surgical strand. Thus, the term "armed suture" includes both so-called "single" and "double" armed sutures. As more clearly illustrated in FIG. 4, the suture package 10 includes a protective envelope or outer container 12 and an inner container 14 which is enveloped and enclosed within the outer container 12.

The outer container 12 consists of two flat sheet-like panel layers 16 and 18 which are of a similar configuration and dimension. Preferably the sheet-like upper panel layer 16 and lower panel layer 18 are rectangular and are sealed together by suitable means known to the art along their periphery 19 as shown in FIG. 1. As a result, the panel layers 16, 18 define therebetween a hermetically sealed region in which the inner container 14 is enclosed. The upper panel layer 16 includes adjacent to one end thereof a window 20 which is constructed of a transparent material so as to allow viewing of the interior region of outer container 12. Each panel layer 16, 18 include a notch, 22 and 24, respectively, which is similarly positioned adjacent the window portion 20. The notches 22 and 24 permit tearing away of the portion of upper and lower panel layers 16, 18 adjacent the window 20. This in turn exposes the inner region defined between the panel layers 16, 18 and, accordingly, the inner container 14 located therein. Alternatively, the upper panel layer 16 can be adapted so as to permit peeling of the upper panel layer 16 away from the lower panel 18.

Preferably the upper and lower panel layers 16, 18 are constructed of a transparent flexible material, e.g., polyethylene or other suitable plastic-like material, which is capable of receiving imprinting thereon. This permits the imprinting of numerous indicia and identifying symbols including, without limitation, identification of the type of suture, the number of sutures contained, the length and color, particularly where color aids in further identifying the type of suture, instructions or directions for use, and any other information to be directed to the user or handler. The plastic composition also permits the panel layers 16, 18 to be sealed together by heat sealing methods. Alternatively, one of the panel layers may be formed of a layer of aluminum foil such as panel layer 18 which would thereby improve the barrier properties of the outer container 12. In yet still another embodiment, either or both panel layers can be formed of a series of two or more overlapping layers of different or similar types of material. For example, lower panel layer 18 may be composed on its outer surface of a clear transparent polyethelene material to receive imprinting as indicated above, while also including an inner facing layer of aluminum foil.

Figure 2:
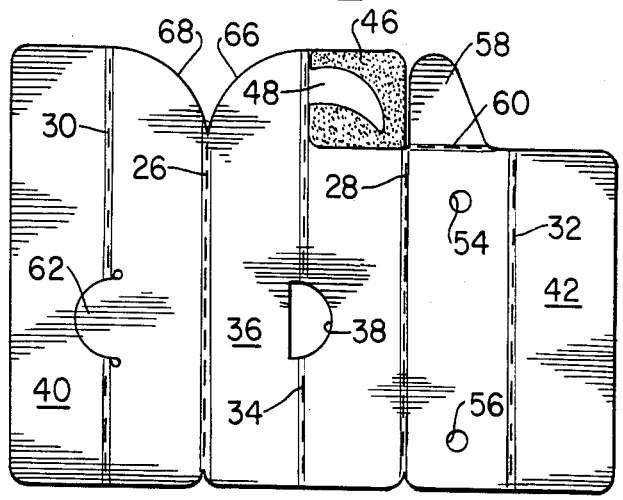
FIG. 2 is a frontal view of the inner suture container in a fully opened or exposed condition.

The inner container 14 is shown in its original unfolded state or exposed condition in FIG. 2 as formed of a flat sheet-like material including a number of score lines 26, 28, 30, 32 and 34. A center panel 36 is formed between score lines 26 and 28 and includes score line 34 positioned centrally of and longitudinally of center panel 36. The center panel 36 also includes a semi-circular cut-out 38 whose purpose will be explained in greater detail hereinbelow.

The center panel 36 is generally rectangular having a longitudinal length aligned with the score lines. Furthermore, the center panel 36 is flanked along both of its longitudinal edges with left and right-hand side panels 40 and 42, respectively. The side panels 40 and 42 are generally rectangular and the left-hand side panel 40 is also of a like dimension and configuration as that of center panel 36. The right-hand side panel 42 has a shorter longitudinal length than either center panel 36 or other side panel 40 for reasons which will become evident below. The side panel 42 is capable of being folded onto itself along score line 32 as illustrated in FIG. 3.

Figure 3:
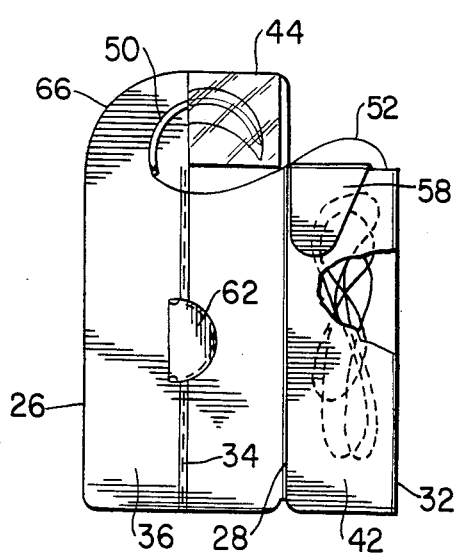
FIG. 3 is a frontal view of the suture container of FIG. 2 in a partially closed condition illustrating the positioning of a suture and its respective needle with respect to the suture container.

The center panel 36 has a window portion 44, as shown in FIG. 3, which is secured adjacent the forward edge of center panel 36. The window portion 44 can be secured to the center panel 36 by a layer of adhesive 46 shown in FIG. 2. The adhesive is omitted from a region beneath the window portion 44 which forms a pocket 48 to receive the sharp-end portion of a needle 50 as shown in FIG. 3. The window 44 permits the viewing of the needle while it is secured within the pocket 48. The layer of adhesive 46 is of such a thickness so as to provide a snug or tight pocket 48 in which the needle is securely held so as to prevent its migrating away from the pocket 48 during storage. Preferably, the window portion is a clear polyfilm. Alternatively, the adhesive 46 can be replaced with a polycoating such that the window portion 44 can be selectively heat sealed to the center panel 36.

Referring now to FIG. 3, a suture 52 is connected to one end of the needle 50 and the major remaining portion of the suture 52 is arranged in a predetermined fashion upon the left-half portion of the right-hand side panel 42 between the score lines 28 and 32. The arrangement of the remaining portion of the suture 52 is such as to prevent entangling or kinking of the major portion of the suture during its withdrawal from the side panel 42. Such arrangements are well known in the art, for example, a figure-eight coil as shown in FIG. 3. To assist in the process of assembling or arranging the suture 52 upon the left-half portion of right-hand side panel 42, two apertures 54 and 56 are provided thereon through which posts (not shown) may be inserted. These posts serve on stops during the arrangement or winding of the suture 52 into the figure-eight configuration.

Thereafter, the right half portion of side panel 42 is folded over along score line 32 onto the left-hand portion so as to enclose the major portion of the suture 52 positioned upon the left-hand portion of side panel 42. The side panel 42 further includes a tab portion 58 which is of a triangular configuration and is foldably secured to the upper edge of side panel 42 by means of a score line 60. The tab 58 is thus capable of being folded back onto the side panel 42 as shown in FIG. 3. Thus, the tab 58 aids in securing the two half portions of side panel 42. In addition, the tab 52 also is of a width dimension less than the width of the left left-half portion of side panel 42. Accordingly, the suture 52 can be pass through the upper edge of side panel 42 as shown in FIG. 3 and thereafter be connected to the end of the needle 50. In this fashion, the thread can only be withdrawn through a limited portion of the upper edge of the left half portion of side panel 42. In turn, such configuration further aids in maintaining the suture 52 in a tangled-free condition during its withdrawal from the right-hand side panel 42. Thereafter, the side panel 42 in its folded condition can again be folded over along score line 28 onto the upper surface of the center panel 36 as shown in FIG. 4.

The left-hand side panel 40 includes a tab 62 which is centrally positioned on the side panel 40 as shown in FIG. 2. Preferably, the tab 62 is integrally formed of the material composing side panel 40. The tab 62 is configured and shaped so as to be able to pass through cutout 38 when the side panel 40 is folded along score line 26 unto the undersurface of center panel 36. In that position, the tab 62 can then be extended through cutout 38 as illustrated in FIG. 3. Upon lifting of the tab 62 the side panel 42 in its folded condition can then be securely held in place atop the upper surface of center panel 36 by extending the tab 62 over and onto the outermost surface of side panel 42 as illustrated in FIG. 4.

Preferably, the center panel 36 and the side panels 40, 42 are integrally constructed of a bleached sulphite board. Furthermore, the composition of the panels is such that they are capable of being sterilized by either irradiation means or by other known sterlizing methods such as employing ethylene oxide.

Figure 4:
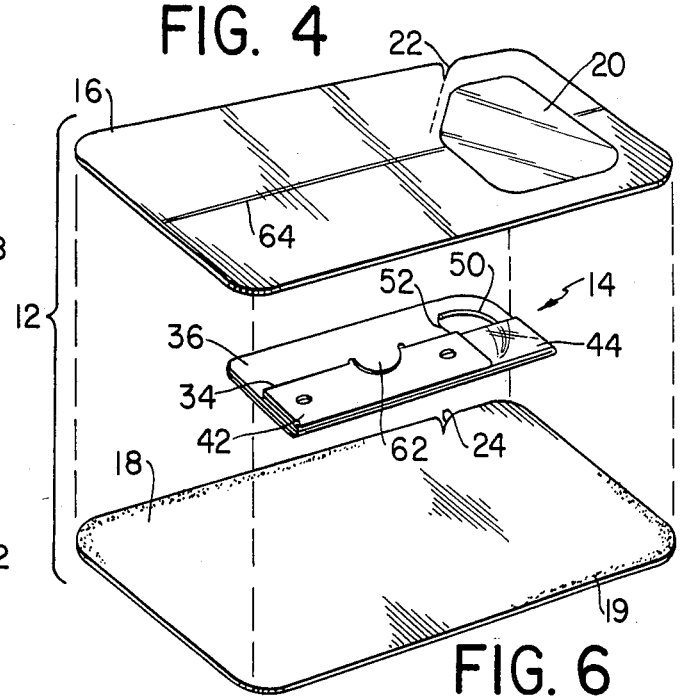
FIG. 4 is an exploded view of the suture package of FIG. 1 illustrating the inner and outer containers in their respective relationships.

Upon folding of the respective panels in the fashion as illustrated in FIG. 4, the inner container 14 is placed between the upper panel layer 16 and the lower panel layer 18 which are thereafter sealed together as indicated above. The inner container 14 is positioned between the layers 16, 18 such that the window 44 is positioned beneath window 20. Preferably, the window 20 is of a larger surface dimension than window 44 and is positioned with respect to window 20 so as to permit viewing of the entire needle 50 and at least a portion of the suture 52 without having to resort to opening a portion of the suture package 10. For this reason, the windows 20 and 44 preferably are constructed of a transparent material such as polyethylene. The inner container 14 is particularly positioned between panel layers 16 and 18 so that score line 34 is aligned with a guide line 64 imprinted on the outer surface of upper panel layer 16 as shown in FIG. 4.

In a preferred embodiment, the corner 66 of center panel 36 adjacent the window 44 is curved to a predetermined shape as well as the adjacent corner 68 of side panel 40 so as to provide a curvilinear configuration, as illustrated in FIG. 3, upon folding of left-hand side panel 40 onto the back surface of center panel 36. The curvilinear configuration is intended to act as a guide during the process of tearing the panel layers 16 and 18 along the notches 22 and 24. In particular, the lower layer panel 18 is separated along the notch 24 but thereafter continues along the curvilinear configuration provided by the center panel 36 and side panel 40. The side panel 40 provides structural integrity to the center panel 36 so as to oppose any degradation of the center panel 36 during the process of removing the panel layer 16, 18 along the notches 22, 24.

Upon sealing of the panel layer 16 and 18 together, the complete suture package 10 is obtained as illustrated in FIG. 1 and is ready for use. After insertion and the sealing of the inner container 14 between the panel layers 16, 18, the suture package can then be sterilized so that the inner container 14 is maintained in a sterile condition throughout its storage. Thereafter, the suture package 10 can be stored indefinitely with the assurance that the sterile environment between the panel layers 16 and 18 is maintained.

In use, the handler, such as a nurse or surgeon, would select a given suture package 10 in accordance with the need of the handler and the information provided on the outer surface of panel layer 16. Moreover, the window 20 as well as window 44 permits the handler to determine if the suture contained therein is of the necessary or desired type. The color of the suture 52 could provide further indentification of the type of suture contained within the suture package 10. Upon selection of a desired suture package 10, the handler would then tear the panel layers 16, 18 along the respective notches 22 and 24. The upper panel layer 16 would tear along notch 22 in a direction generally transversely toward the guide line 64. Simultaneously the lower panel layer 18 would tear along the notch 24 inwardly toward the center of the panel layer 18 until the tear reaches the leading edge of inner container 14. At that point, the lower panel layer 18 continues to tear in a curvilinear direction along the outer curved edge 66 of center panel 36.

Figure 5:
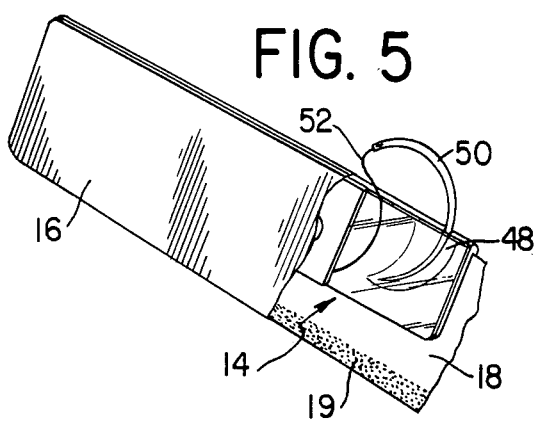
FIG. 5 is a perspective view of the suture package of FIG. 1 in an open condition for dispensing of the suture contained therein.

Thereafter the suture package is folded in its entirety along the guide line 64 of the suture package 10. At the same time, the inner container is folded along score line 34. As a result, the needle portion extending outwardly of the pocket 48 is exposed and stands free of the upper surface of center panel 36 together with a portion of the suture 52 as illustrated in FIG. 5. The suture package 10 need only be partially folded along guide line 62 in order that the aforementioned needle portion be exposed free of the center panel 36.

In this fashion, the needle can be easily grasped with a pair of typical needle holders either by a right or left-handed handler. The dispensing of the needle and suture, therefore, is obtained from the suture package 10 in an efficient and expeditious manner.

Figure 6:
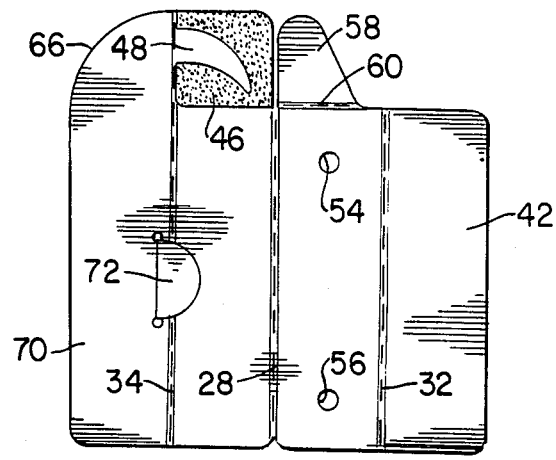
FIG. 6 is a frontal view of an alternative embodiment of the inner container of FIG. 2.

An alternative embodiment of the inner container 14 according to the present invention is illustrated in FIG. 6 and includes essentially the same elements as illustrated in FIG. 2. Accordingly, the description, both structural and functional, presented above with respect to these same elements is applicable here as well and, therefore, is not repeated. The embodiment illustrated in FIG. 6 is generally identical in all respects to that illustrated in FIG. 2 but for the side panel 40 which is not included. In order to maintain the rigidity necessary to preserve the integrity of the center panel 70 during the tearing away of the upper and lower panel layers 16, 18, the center panel 70 preferably is formed of a suitably thicker material than that employed for the embodiment illustrated in FIG. 2. Alternatively, the center panel 70 can be reinforced according to known methods in the region adjacent the curved edge 66.

In addition, center panel 70 differs from center panel 36 of FIG. 2 in that the cutout 38 for center panel 36 is replaced by a tab 72 which functions in the same fashion as does tab 62 shown in FIG. 3. For this reason, no further discussion or description of the embodiment of FIG. 6 is believed necessary.

The above-described inner container 14 is not limited as to the number of sutures 52 and corresponding needles 50 which can be retained thereby. In this regard, a series of pockets 48 can be formed under the window 20 to receive the desired number of needles 50. Accordingly, the corresponding sutures 52 are separately retained by the right-hand panel so that any individual needle and respective suture can be withdrawn without disturbing the remaining needles and sutures.

We claim:

1. A suture dispensing apparatus comprising:
   a. at least one suture including at least one needle and strand secured to one end of the needle;
   b. first panel means including pocket means retaining a first sharp-end portion of the needle in a snug fitting relationship, said pocket means being configured and dimensioned so as to permit selective withdrawal of said first sharp-end portion of the needle free of said pocket means, said first panel means having a first longitudinal score line extending across the second or remaining portion of the needle along a predetermined longitudinal axis such that the second or remaining portion of the needle is exposed free of said first panel means upon folding of said first panel means along said first longitudinal score line while said pocket means retains the first sharp-end portion of the needle; and
   c. second panel means for retaining a major portion of the strand, said second panel means being foldably secured to said first panel means along respective longitudinal edges thereof parallel to said first score line and configured such that the strand can be withdrawn therefrom upon removal of the first sharp-end portion of the needle from said first panel means, said second panel means having a second longitudinal score line such that said second panel means encloses a portion of the strand upon folding of said second panel means back upon itself along said second score line, and said second panel means in said folded condition being capable of being folded over along its longitudinal edge so as to overlap a surface portion of said first panel means with said second longitudinal score line aligned with said first score line.

2. An apparatus for dispensing at least one suture comprising:
   a. at least one suture including at least one needle and strand secured to one end of the needle;
   b. first panel means including pocket means retaining a first sharp-end portion of the needle in a snug fitting relationship, said pocket means being configured and dimensioned so as to permit selective withdrawal of said first sharp-end portion of the needle free of said pocket means, said first panel means having a first longitudinal score line extending across the second or remaining portion of the needle along a predetermined longitudinal axis such that the second or remaining portion of the needle is exposed free of said first panel means upon folding of said first panel means along said first longitudinal score line while said pocket means retains the first sharp-end portion of the needle; and
   c. second panel means for retaining a major portion of the strand and configured such that the strand can be withdrawn therefrom upon removal of the first sharp-end portion of the needle from said first panel means, said second panel means being foldably connected to said first panel means along respective longitudinal edges thereof parallel to said first score line, said second panel means having a second longitudinal score line such that said second panel means encloses the major portion of the strand upon folding of said second panel means back upon itself along said second score line, and said second panel means in said folded condition enclosing the major portion of the strand being capable of being folded over along its longitudinal edge connected to said first panel means so as to overlap a surface portion of said first panel means with said second longitudinal score line aligned with said first score line.

3. A suture dispensing apparatus comprising:
   a. at least one suture including at least one needle and strand secured to one end of the needle;
   b. first panel means including pocket means securely retaining a first sharp-end portion of the needle in a snug fitting relationship, said pocket means being configured and dimensioned so as to permit selective withdrawal of said first sharp-end portion of the needle free of said pocket means, said first panel means having a first longitudinal score line extending across the second or remaining portion of the needle along a predetermined longitudinal axis such that the second or remaining portion of the needle is exposed free of said first panel means upon folding of said first panel means along said first longitudinal score line while said pocket means retains the first sharp-end portion of the needle; and
   c. second panel means for securely retaining a major portion of the strand, said second panel means being foldably secured to said first panel means along respective longitudinal edges thereof which are parallel to said first score line and configured such that the strand can be withdrawn therefrom upon removal of the first sharp-end portion of the needle from said first panel means, said second panel means having a second longitudinal score line such that said second panel means encloses a portion of the strand upon folding of said second panel means back upon itself along said second score line, and said second panel means in said folded condition being capable of being folded over along its longitudinal edge so as to overlap a surface portion of said first panel means with said second longitudinal score line aligned with said first score line.

4. The apparatus according to claim 3 wherein said retaining means includes a window portion permitting viewing of said first sharp-end portion of the needle retained in secured relationship with said first panel means.

5. The apparatus according to claim 4 wherein said window portion is constructed of transparent material.

6. The apparatus according to claim 5 wherein said first and said second panel means are of a generally rectangular configuration.

7. The apparatus according to claim 6 wherein said firsr and said second panel means are foldably secured to each other along respective longitudinal edges thereof, said longitudinal edges being aligned with said predetermined axis.

8. The apparatus according to claim 7 wherein said second panel means is capable of being folded along its longitudinal axis such that said second panel means encloses the major portion of the suture upon folding of said second panel means back upon itself along its longitudinal axis.

9. The apparatus according to claim 8 further including a tab portion extending outwardly from a peripheral edge of said second panel means, said tab capable of being folded back onto said second panel means so as to guide the major portion of the suture during its withdrawal from said second panel means.

10. The apparatus according to claim 9 wherein said second panel means in its folded condition enclosing the major portion of the suture is folded over along its longitudinal edge connected to said first panel means so as to overlap a surface portion of said first panel means.

11. The apparatus according to claim 10 further including third panel means foldably secured along one longitudinal edge to the other longitudinal edge of said first panel means.

12. The apparatus according to claim 11 wherein said first, second and third panel means are integrally constructed of a bleached sulphite board.

13. The apparatus according to claim 3 wherein said first and second panel means are integrally constructed of a bleached sulphite board.

14. The apparatus according to either of claim 13 or 12 wherein said second panel means includes means for maintaining the major portion of the suture in a predetermined configuration so as to prevent entangling or kinking of the major portion of the suture during dispensing of the suture therefrom.

15. The apparatus according to claim 14 wherein said panel means are capable of being sterilized by at least one of irradition and ethylene oxide sterilizing methods.

16. A suture dispensing apparatus comprising:
  a. at least one suture including at least one needle and strand secured to one end of the needle;
  b. first panel means including pocket means securely retaining a first sharp-end portion of the needle in a snug fitting relationship, said pocket means being configured and dimensioned so as to permit selective withdrawal of said first sharp-end portion of the needle free of said pocket means, said first panel means having a longitudinal score line extending across the second or remaining portion of the needle such that the second or remaining portion of the needle is exposed free of said first panel means upon folding of said first panel means along said longitudinal score line while said pocket means retains the first sharp-end portion of the needle; and
  c. second panel means for securely retaining a major portion of the strand, said second panel means being foldably secured to said first panel means along respective longitudinal edges thereof which are parallel to said score line and configured such that the strand can be withdrawn therefrom upon removal of the first sharp-end portion of the needle from said first panel means;
  d. said first panel means including a window portion constructed of transparent material permitting viewing of the needle retained in secured relationship with said first panel means, said first and said second panel means being of a generally rectangular configuration and being foldably secured to each other along respective longitudinal edges thereof, said longitudinal edges being aligned with said predetermined axis, said second panel means being capable of being folded along its longitudinal axis such that said second panel means encloses the major portion of the suture upon folding of said second panel means back upon itself along its longitudinal axis;
  e. a tab portion extending outwardly from a peripheral edge of said second panel means, said tab capable of being folded back onto said second panel means so as to guide the major portion of the suture during its withdrawal from said second panel means, said second panel means in its folded condition enclosing the major portion of the suture being folded over along its longitudinal edge connected to said first panel means so as to overlap a surface portion of said first panel means; and
  f. third panel means foldably secured along one longitudinal edge to the other longitudinal edge of said first panel means, an aperture positioned centrally of said first panel means and a tab centrally formed of said third panel means, such that upon folding of said third panel means onto the surface of said first panel means opposite said second panel means, said tab is capable of extending through said aperture so as to overlie at least a portion of said second panel means and therefore secure said second panel means after said second panel means has been folded onto said third panel means.

17. A device for storing and dispensing a suture comprising:
  a. at least one suture including at least one needle and strand secured to one end of the needle;
  b. outer container means including a first panel layer and a second panel layer of like configuration and dimension, said first and second panel layers being secured together along their peripheries so as to define an enclosed region therebetween, said first panel layer including a first window portion permitting viewing of said enclosed region;
  c. inner container means positioned within said region including:
    (1) first panel means including pocket means securely retaining at least a substantial first sharp-end portion of the needle such that the needle is maintained in a secured snug fitting relationship with said first panel means, said procket means being configured and dimensioned so as to permit withdrawal of said first sharp-end portion of the needle free of said pocket means, said first panel means having a first longitudinal score line extending across the second or remaining portion of the needle along a predetermined longitudinal axis in the plane of said first panel means such that the second or remaining portion of the needle is exposed free of said first panel means upon folding of said first panel means along said first longitudinal score line while said pocket means securely retains the first sharp-end portion of the needle, said pocket means including a second window portion positioned in relation to said first window portion so as to permit viewing of the needle retained in secured snug fitting relationship with said first panel means; and
    (2) second panel means for securely retaining a major portion of the strand, said second panel means being foldably secured to said first panel means along respective longitudinal edges thereof which are parallel to said first score line and configured such that the strand can be withdrawn therefrom upon removal of the first sharp-end portion of the needle from said first panel means, said second panel means having a second longitudinal score line such that said second panel means encloses a portion of the strand upon folding of said second panel means back upon itself along said second score line, and said second panel means in said folded condition being capable of being folded over along its longitudinal edge so as to overlap a surface portion of said first panel means with said second longitudinal score line aligned with said first score line.

18. The device according to claim 17 wherein said first window portion is of a larger surface dimension than said second window portion.

19. The device according to claim 18 wherein said first window portion overlies said second window portion such that the entire needle together with at least a portion of the suture can be viewed through said first and said second window portions.

20. The device according to claim 19 wherein said first and second window portions are constructed of transparent material.

21. The device according to claim 20 wherein said first panel layer and said second panel layer each include a similarly positioned notch so as to permit tearing and removal of said first and second panel layers adjacent said first window portion.

22. The device according to claim 21 wherein said first and said second panel layers are each of a generally rectangular configuration.

23. The device according to claim 22 wherein said first and said second panel layers are constructed of a clear polyester capable of being imprinted so as to provide numerical and identifying indicia thereon.

24. The device according to claim 23 wherein said second panel layer includes a layer of metallic foil.

25. The device according to claim 24 wherein said first and said second panel layers are capable of being sterilized by at least one of irradition and ethylene oxide sterilizing methods.

26. The device according to claim 17 wherein said first and said second panel means are of a generally rectangular configuration and are configured and dimensioned so as to be capable of being enclosed within said region defined between said first and said second panel layers.

27. The device according to claim 26 wherein said first and second panel means are secured to each other along respective longitudinal edges thereof, said longitudinal edges being aligned with said predetermined axis.

28. The device according to claim 27 wherein said second panel means is capable of being folded along its longitudinal axis such that second panel means encloses the major portion of the suture thread upon folding of said second panel means back upon itself along its longitudinal axis.

29. The device according to claim 28 further including a tab portion extending outwardly from a peripheral edge of said second panel means, said tab capable of being folded back onto said second panel means so as to guide the major portion of the suture during its withdrawal from said second panel means.

30. The device according to claim 29 wherein said sec and panel means in its folded condition enclosing the major portion of the suture is folded over along its longitudinal edge connected to said first panel means so as to overlap a surface portion of said first panel means.

31. The device according to claim 30 wherein said first and said second panel means are constructed of a bleached sulphite board.

32. The device according to claim 31 wherein said second panel means includes means for maintaining the major portion of the suture in a predetermined configuration so as to prevent entangling or kinking of the major portion of the suture during dispensing of the suture therefrom.

33. The device according to claim 32 wherein said first and said second panel means are capable of being sterilized by at least one of irradition and ethylene oxide sterilizing methods.

34. The container according to claim 33 wherein a corner of said first panel means adjacent said second window portion is generally curvilinearly configured such that said second layer panel upon being torn away adjacent said first window portion separates along said curvilinear configuration.

35. A method of dispensing a suture comprising:
a. taking a device for storing and dispensing a suture and needle, said device including:
(1) at least one suture including at least one needle and strand secured to one end of the needle;
(2) outer container means including a first panel layer and a second panel layer of like configuration and dimension, said first and second panel layers being secured together along their peripheries so as to define an enclosed region therebetween, said first panel layer including a first window portion so as to permit viewing of said enclosed region;
(3) inner container means positioned within said region including:
  (a) first panel means including pocket means securely retaining at least a substantial first sharp-end portion of the needle such that the needle is maintained in a secured snugfitting relationship with said first panel means, said pocket means being configured and dimensioned so as to permit selective withdrawal of said first sharp-end portion of the needle free of said pocket means, said first panel means having a first longitudinal score line extending across the second or remaining portion of the needle along a predetermined longitudinal axis in the plane of said first panel means such that the second or remaining portion of the needle is exposed free of said first panel means upon folding of said first panel means along said first longitudinal score line while said pocket means securely retains the first portion of the needle, said pocket means including a second window portion positioned in relation to said first window portion so as to permit viewing of the needle retained in secured relationship with said first panel means; and
  (b) second panel means for securely retaining a major portion of the strand, said second panel means being foldably secured to said first panel means along respective longitudinal edges thereof which are parallel to said first score line and configured such that the strand can be withdrawn therefrom upon removal of the first sharp-end portion of the needle from said first panel means, said second panel means having a second longitudinal score line such that said second panel means encloses a portion of the strand upon folding of said second panel means back upon itself along said second score line, and said second panel means in said folded condition being capable of being folded over along its longitudinal edge so as to overlap a surface portion of said first panel means with said second longitudinal score line aligned with said first score line;

b. tearing a portion of said first and second panel layers away therefrom so as to expose the needle and at least a portion of the strand connected thereto;

c. folding said device along said predetermined longitudinal axis; and d. withdrawing the needle from said second window portion and thereafter withdrawing the strand from said inner container.

* * * * *